US011028406B2

(12) United States Patent
Malnoy et al.

(10) Patent No.: US 11,028,406 B2
(45) Date of Patent: Jun. 8, 2021

(54) PODOSPHAERA LEUCOTRICHA RESISTANCE PROVIDING GENES IN MALUS DOMESTICA

(71) Applicant: Fondazione Edmund Mach, San Michele all'Adige (IT)

(72) Inventors: Mickael Malnoy, San Michele all'Adige (IT); Stefano Pessina, Monza (IT); Riccardo Velasco, Nogaredo (IT); Dario Angeli, San Michele all'Adige (IT); H. J. Schouten, Wageningen (NL)

(73) Assignee: Fondazione Edmund Mach, San Michele all'Adige (IT)

( * ) Notice: Subject to any disclaimer, the term of this patent is extended or adjusted under 35 U.S.C. 154(b) by 396 days.

(21) Appl. No.: 15/765,752

(22) PCT Filed: Oct. 5, 2016

(86) PCT No.: PCT/EP2016/073783
§ 371 (c)(1),
(2) Date: Apr. 4, 2018

(87) PCT Pub. No.: WO2017/060294
PCT Pub. Date: Apr. 13, 2017

(65) Prior Publication Data
US 2018/0298403 A1 Oct. 18, 2018

(30) Foreign Application Priority Data
Oct. 7, 2015 (WO) .................. PCT/EP2015/073135

(51) Int. Cl.
*C12N 15/82* (2006.01)
*C07K 14/415* (2006.01)
(52) U.S. Cl.
CPC ........ *C12N 15/8282* (2013.01); *C07K 14/415* (2013.01); *C12N 15/8218* (2013.01)
(58) Field of Classification Search
None
See application file for complete search history.

(56) References Cited

FOREIGN PATENT DOCUMENTS

CN 104561027 A 4/2015

OTHER PUBLICATIONS

Pessina, et al. (BMC genomics 15.1 (2014): 618). (Year: 2014).*
Abbott et al., "Simultaneous Suppression of Multiple Genes by Single Transgenes. Down-Regulation of Three Unrelated Lignin Biosynthetic Genes in Tobacco", Plant Physiology, 2002, p. 844-853, vol. 128.
Acevedo-Garcia et al., "Magical mystery tour: MLO proteins in plant immunity and beyond", New Phytologist, 2014, p. 273-281, vol. 204.
Angeli et al., "Is the mycoparasitic activity of Ampelomyces quisqualis biocontrol strains related to phylogeny and hydrolytic enzyme production?", Biological Control, 2012, p. 348-358, vol. 63.
Bai et al., "Naturally Occurring Broad-Spectrum Powdery Mildew Resistance in a Central American Tomato Accession is Caused by Loss of Mlo Function", Molecular Plant-Microbe Interactions, 2008, p. 30-39, vol. 21:1.
Bari et al., "Role of plant hormones in plant defence responses", Plant Molecular Biology, 2009, p. 473-488, vol. 69.
Baudoin et al., "QoI Resistance of Plasmopara viticola and Erysiphe necator in the Mid-Atlantic United States", Plant Health Progess, 2008, p. 1-8.
Botton et al., "Signaling Pathways Mediating the Induction of Apple Fruitlet Abscission", Plant Physiology, 2011, p. 185-208, vol. 155.
Bruce et al., "Plant defence signalling induced by biotic attacks", Plant Biology, 2007, p. 387-392, vol. 10.
Buschges et al., "The Barley Mlo Gene: A Novel Control Element of Plant Pathogen Resistance", Cell, 1997, p. 695-705, vol. 88.
Campbell et al., "Introduction to Plant Disease Epidemiology", 1990, p. 4-19, John Wiley and Sons, Hoboken, NJ.
Chen et al., "Two Seven-Transmembrane Domain Mildew Resistance Locus O Proteins Cofunction in *Arabidopsis* Root Thigmomorphogenesis", The Plant Cell, 2009, p. 1972-1991, vol. 21.
Chowdhury et al., "Differential accumulation of callose, arabinoxylan, and cellulose in nonpenetrated versus penetrated papillae on leaves of barley infected with *Blumeria graminis* f. sp. *hordei*", New Phytologist, 2014, p. 650-660, vol. 204.
Consonni et al., "Conserved requirement for a plant host cell protein in powdery mildew pathogenesis", Nature Genetics, 2006, p. 716-720, vol. 38:6.
Dufour et al., "Assessment of fungicide resistance and pathogen diversity in Erysiphe necator using quantitative real-time PCR assays", Pest Management Science, 2011, p. 60-69, vol. 67.
Feechan et al., "Identification of grapevine MLO gene candidates involved in susceptibility to powdery mildew", Functional Plant Biology, 2008, p. 1255-1266, vol. 35.
Feechan et al., "Mechanisms of powdery mildew resistance in the Vitaceae family", Molecular Plant Pathology, 2011, p. 263-274, vol. 12:3.
Hellemans et al., "qBase relative quantification framework and software for management and automated analysis of real-time quantitative PCR data", Genome Biology, 2007, p. 1-19, vol. 8.
Huckelhoven, "The effective papilla hypothesis", New Phytologist, 2014, p. 438-440, vol. 204.
Jorgensen, "Discovery, characterization and exploitation of Mlo powdery mildew resistance in barley", Euphytica, 1992, p. 141-152, vol. 63.

(Continued)

*Primary Examiner* — Charles Logsdon
(74) *Attorney, Agent, or Firm* — The Webb Law Firm

(57) ABSTRACT

Provided herein are *Podosphaera leucotricha* resistance conferring genes, plants, plant parts and seeds comprising the present resistance providing genes and the use thereof for selecting *Podosphaera leucotricha* resistant plants. Specifically, the present invention relates to *Podosphaera leucotricha* resistance conferring genes, wherein the amino acid sequence encoded by said resistance conferring genes is the primary amino acid sequence represented SEQ ID No. 1, or a primary amino acid sequence with more than 70% identity, preferably more than 80% identity, more preferably more than 90% identity, and most preferably more than 95% identity with SEQ ID No. 1; and wherein said resistance conferring gene is impaired.

7 Claims, 6 Drawing Sheets

Specification includes a Sequence Listing.

(56) References Cited

OTHER PUBLICATIONS

Joshi et al., "Functional analysis and expression profiling of HcrVf1 and HcrVf2 for development of scab resistant cisgenic and intragenic apples", Plant Molecular Biology, 2011, p. 579-591, vol. 75.

Ling et al., "Robust RT-qPCR Data Normalization: Validation and Selection of Internal Reference Genes during Post-Experimental Data Analysis", PLoS ONE, 2011, p. 1-8, vol. 6:3.

Lyngkjaer et al., "The Barley mlo-gene: an important powdery mildew resistance source", EDP Sciences, 2000, p. 745-756, vol. 20:7.

Madden et al., "Spatial Aspects of Epidemics-III: Patterns of Plant Disease", The Study of Plant Disease Epidemics, 2007, p. 235-278.

Miklis et al., "Barley MLO Modulates Actin-Dependent and Actin-Independent Antifungal Defense Pathways at the Cell Periphery", Plant Physiology, 2007, p. 1132-1143, vol. 144.

Panstruga, "Serpentine plant MLO proteins as entry portals for powdery mildew fungi", Biochemical Society Transactions, 2005, p. 389-392, vol. 33:2.

Parlevliet, "What Is Durable Resistance, A General Outline", Durability of disease resistance, 1993, p. 23-39.

Pavan et al., "Loss of susceptibility as a novel breeding strategy for durable and broad-spectrum resistance", Molecular Breeding, 2010, p. 1-12, vol. 25.

Pavan et al., "Pea powdery mildew er1 resistance is associated to loss-of-function mutations at a MLO homologous locus", Theoretical and Applied Genetics, 2011, p. 1425-1431, vol. 123.

Pessina et al., "Characterization of the MLO gene family in Rosaceae and gene expression analysis in Malus domestica", BMC Genomics, 2014, p. 1-12, vol. 15:618.

Pessina et al., "Knockdown of MLO genes reduce susceptibility to powdery mildew in grapevine", Horticulture Research, 2016, p. 1-9, vol. 3.

Reinstadler et al., "Novel induced mlo mutant alleles in combination with site-directed mutagenesis reveal functionally important domains in the heptahelical barely Mlo protein", BMC Plant Biology, 2010, p. 1-13, vol. 10:31.

Robert-Seilaniantz et al., "Pathological hormone imbalances", Plant Biology, 2007, p. 372-379, vol. 10.

Stolzenburg et al., "The role of papillae in resistance to powdery mildew conditioned by the ml-o gene in barley. I Correlative evidence", Physiological Plant Pathology, 1984, p. 337-346, vol. 25.

Turecheck et al., "Powdery Mildew of Apple", NYSIPM Cornell University, 2004, p. 1-3.

Vanacker et al., "Early H2O2 Accumulation in Mesophyll Cells Leads to Induction of Glutathione during the Hyper-Sensitive Response in the Barley-Powdery Mildew Interaction", Plant Physiology, 2000, p. 1289-1300, vol. 123.

Wightwick et al., "Environmental Risks of Fungicides Used in Horticultural Production Systems", Fungicides, 2010, p. 273-304.

Winterhagen et al., "Transcriptional Up-Regulation of Grapevine MLO Genes in Response to Powdery Mildew Infection", American Journal of Enology and Viticulture, 2008, p. 159-168, vol. 59:2.

Zheng et al., "Loss of Function in Mlo Orthologs Reduces Susceptibility of Pepper and Tomato to Powdery Mildew Disease Caused by Leveillula taurica", PLOS ONE, 2013, p. 1-14, vol. 8:7.

* cited by examiner

A. Gala

B. Gala

C. TG0 100X

D TG11+19 200X

SEQUENCE LISTING

<160> NUMBER OF SEQ ID NOS: 17

<210> SEQ ID NO 1
<211> LENGTH: 589
<212> TYPE: PRT
<213> ORGANISM: Malus sp.

<400> SEQUENCE: 1

Met Ala Gly Gly Lys Lys Gly Arg Ser Leu Glu Gln Thr Pro Thr Trp
1               5                   10                  15

Ala Val Ala Val Val Cys Phe Val Leu Val Leu Ile Ser Ile Leu Ile
            20                  25                  30

```
Glu Tyr Phe Ile His Leu Ile Gly Lys Trp Leu Lys Lys Arg Asn Lys
         35                  40                  45
Arg Ala Leu Tyr Glu Ala Leu Glu Lys Ile Lys Ser Glu Leu Met Leu
 50                  55                  60
Leu Gly Phe Leu Ser Leu Leu Thr Val Gly Gln Gly Pro Ile Ser
 65                  70                  75                  80
Asn Ile Cys Ile Ser Lys Ala Val Gly Ala Thr Trp His Pro Cys Ser
                     85                  90                  95
Lys Lys Gln Glu Val Lys Ser Asp Lys Asn Glu Asp Lys Ser Ser Val
                 100                 105                 110
Ser Asp Asp Asn Ala Arg Arg Leu Leu Ser Ala Leu Asp Ser Ser
                 115                 120                 125
Gly Gly Gly Arg Arg Val Leu Ala Ala Ala Gly Tyr Asp Lys Cys Ala
 130                 135                 140
Ala Lys Asn Lys Val Pro Phe Val Ser Tyr Tyr Gly Ile His Gln Leu
145                 150                 155                 160
His Ile Leu Ile Phe Val Leu Ala Val Phe His Val Leu Tyr Cys Ile
                 165                 170                 175
Thr Thr Leu Val Leu Gly Arg Ala Lys Met Arg Lys Trp Lys Thr Trp
                 180                 185                 190
Glu Leu Glu Thr Lys Thr Ala Ala Tyr Gln Phe Ser His Asp Pro Glu
                 195                 200                 205
Arg Phe Arg Phe Ala Arg Asp Thr Ser Phe Gly Arg Arg His Leu Ser
                 210                 215                 220
Phe Trp Ser Arg Ser Pro Ile Ser Leu Trp Ile Val Cys Phe Phe Arg
225                 230                 235                 240
Gln Phe Val Arg Ser Val Pro Lys Val Asp Tyr Leu Thr Leu Arg His
                 245                 250                 255
Gly Phe Ile Ala Ala His Leu Ala Pro Gln Ser Gln Thr Lys Phe Asp
                 260                 265                 270
Phe Gln Lys Tyr Ile Asn Arg Ser Leu Glu Glu Asp Phe Lys Val Val
                 275                 280                 285
Val Gly Ile Ser Pro Thr Ile Trp Leu Phe Ala Val Leu Ile Leu Met
                 290                 295                 300
Ser Asn Thr His Gly Ser Arg Ser Tyr Leu Trp Leu Pro Phe Val Pro
305                 310                 315                 320
Leu Val Met Ile Leu Met Val Gly Thr Lys Leu Gln Val Ile Ile Thr
                 325                 330                 335
Lys Met Gly Leu Lys Leu Ser Glu Arg Gly Glu Val Val Arg Gly Thr
                 340                 345                 350
Pro Leu Val Glu Pro Gly Asp His Leu Phe Trp Phe Asn Asn Pro Arg
                 355                 360                 365
Leu Leu Leu Tyr Ile Ile His Phe Val Leu Phe Gln Asn Ala Phe Ala
 370                 375                 380
Leu Ala Phe Phe Ala Trp Thr Trp Ser Gly Lys Gly Gly Leu His Phe
385                 390                 395                 400
Thr Leu Leu Gln Tyr Glu Phe Gly Leu Lys Ser Cys Phe His Glu Lys
                 405                 410                 415
Leu Glu Asp Val Val Leu Arg Ile Ser Met Gly Val Ile Ile Gln Ile
                 420                 425                 430
Leu Cys Ser Tyr Val Thr Leu Pro Leu Tyr Ala Leu Val Thr Gln Met
                 435                 440                 445
```

| | | | | | | | | | | | | | | |
|---|---|---|---|---|---|---|---|---|---|---|---|---|---|---|
|Gly|Ser|Thr|Met|Lys|Pro|Val|Ile|Phe|Asn|Asp|Arg|Val|Ala|Thr|Ala|
| |450| | | |455| | | |460| | | | | |

Gly Ser Thr Met Lys Pro Val Ile Phe Asn Asp Arg Val Ala Thr Ala
            450             455             460

Leu Lys Lys Trp His Ile Ala Ala Lys Lys His Val Lys His Lys Asn
465             470             475             480

Ala Ser Pro Ala Ser Ala Pro Gly Thr Pro Leu His Ser Met Ser Pro
            485             490             495

Val His Leu Leu Arg Asn Tyr Lys Tyr Glu Gln Asp Ile Asp Ser Ile
            500             505             510

Gln Thr Ser Pro Arg Met Pro Tyr Phe Asp Asn Glu Gly Ser Asp Ser
            515             520             525

Pro Phe His His Gln Asp Asn Leu Thr Trp Ser Gln Gln Gly Thr Asn
530             535             540

Met Glu Gly Gln Lys Glu Glu Ile Ser Ala His Gly Pro Asn Ala Glu
545             550             555             560

Ser Asn Ala Leu Gly Ala Tyr Gly Ser Ile Ile Gln His Glu Ile Gln
            565             570             575

Ile His Ser Ala Ala Leu Thr Phe Glu Lys Thr Glu Arg
            580             585

<210> SEQ ID NO 2
<211> LENGTH: 1733
<212> TYPE: DNA
<213> ORGANISM: Malus sp.

<400> SEQUENCE: 2

```
atggagcaac ttggcatcca tgcagtaaga agcaagaggt caaatcagac aagaacgaag      60
ataagagtag tgtttcagat gacaacgccc gcagaaggct ctctcagcc ttggattcca     120
gtggggtgg ccgacgtgtt ttagcagctg ctggatatga caatgtgct gccaaggtaa     180
tttgtgtcat attatgggat ccaccagctt cacatactca tctttgtgct agccgtcttc     240
cacgtgcttt actgcataac aaccctagtt ttgggcagag caaaggtctc tctctcgaaa     300
acatgggaac tggaaacaaa acagctgct accaattctc acatggcagg aggaaaaaaa     360
ggaagatctt tggagcaaac accaacttgg gcagttgccg tgtttgtttc gttttggttt     420
tatttcaatt ctcatcgaat atttcattca tttaattgga aaggtgttga aaagagaaa      480
caaaagagct ctctatgaag cacttgagaa gatcaagtcg agcttatgct attagggttc     540
ctatccttgc ttctaacagt aggacaaggc cccatttcaa atatttgtat atcgaaggct     600
gttggtatgc tacctcagat ttgccagaga cacatccttt gggagaagac acttgagctt     660
ttggagccgt tctcccatta gcttatggat tgtaagagtt gaaaattgta agatctgtgc     720
ccaaagttga ttacttgact ctgcgacatg ggtttattgc gtaagtctct tactaaattt     780
aaactaagtt tgacttccag aagtacatta acaggtcact tgaagaggat ttcaaggttg     840
tcgtagggat caggtgggtc actagtctag gcatactcat gtcaaacacc cacggtaagc     900
ttcccttac ttgctaacct gttttccccc tagttgtaag cgccaaccc accgttcaat     960
ccttttttaat aacaaagatg gggctcaaat tatcagaaag aggtgaagtg ttaggggaa    1020
ccccactggt tgagcctggt gaccatctct tctggttcaa caaccccga ctcctgcttt    1080
atatcatcca ctttgttctc ttcaggtaat tcactttctt tccaattgga tttagtgatt    1140
gtaagtaaaa ctgtaaaccc atatttactt tcacggatga atttggcttg aagtcttgct    1200
tccatgagaa gttggaagat gtcgttttaa gaatatcaat ggggtaactc aaattatttt    1260
tacatttttt ttgttcactc ctctttatgc attggtaaca caggtaatta agtggccatg    1320
```

-continued

| | |
|---|---|
| atgaaaatta gatgctaaaa agtggcgact gcacttaaaa aatggcacat tgcagcgaag | 1380 |
| aagcacgtaa acacaagaa tgcaagtcca gccagtgcac caggcactcc tttgcactcc | 1440 |
| atgtcccctg ttcatctact acgcaactat aaatatgaac aagacattga cagcattcag | 1500 |
| acatcaccaa gaatgcctta ttttgataac gaaggttcag actcaccgtt tcatcaccaa | 1560 |
| gacaatttga cttggtctca gcaaggtaca acatggagg gtcagaagga ggagattagt | 1620 |
| gctcatggac taacgcaga gagcaatgct ttaggcgctt atggttcgat aattcaacat | 1680 |
| gagattcaaa ttcactcggc ggcactcaca tttgagaaaa cagaaagagc tga | 1733 |

<210> SEQ ID NO 3
<211> LENGTH: 22
<212> TYPE: DNA
<213> ORGANISM: Artificial Sequence
<220> FEATURE:
<223> OTHER INFORMATION: EF1 Forward Primer

<400> SEQUENCE: 3
tactggaaca tcacaggctg ac                                              22

<210> SEQ ID NO 4
<211> LENGTH: 22
<212> TYPE: DNA
<213> ORGANISM: Artificial Sequence
<220> FEATURE:
<223> OTHER INFORMATION: EF1 Reverse Primer

<400> SEQUENCE: 4
tggacctctc aatcatgttg tc                                              22

<210> SEQ ID NO 5
<211> LENGTH: 20
<212> TYPE: DNA
<213> ORGANISM: Artificial Sequence
<220> FEATURE:
<223> OTHER INFORMATION: Ubiquitin Forward Primer

<400> SEQUENCE: 5
catcccccca gaccagcaga                                                 20

<210> SEQ ID NO 6
<211> LENGTH: 21
<212> TYPE: DNA
<213> ORGANISM: Artificial Sequence
<220> FEATURE:
<223> OTHER INFORMATION: Ubiquitin Reverse Primer

<400> SEQUENCE: 6
accacggaga cgaagcacca a                                               21

<210> SEQ ID NO 7
<211> LENGTH: 20
<212> TYPE: DNA
<213> ORGANISM: Artificial Sequence
<220> FEATURE:
<223> OTHER INFORMATION: Md8283 Forward Primer

<400> SEQUENCE: 7
ctcgtcgtct tgttccctga                                                 20

<210> SEQ ID NO 8
<211> LENGTH: 22
<212> TYPE: DNA
<213> ORGANISM: Artificial Sequence

```
<220> FEATURE:
<223> OTHER INFORMATION: Md8283 Reverse Primer

<400> SEQUENCE: 8
gcctaaggac aggtggtcta tg                                               22

<210> SEQ ID NO 9
<211> LENGTH: 20
<212> TYPE: DNA
<213> ORGANISM: Artificial Sequence
<220> FEATURE:
<223> OTHER INFORMATION: MdMLO11 Forward Primer

<400> SEQUENCE: 9
atcgaaggct gttggagcaa                                                  20

<210> SEQ ID NO 10
<211> LENGTH: 20
<212> TYPE: DNA
<213> ORGANISM: Artificial Sequence
<220> FEATURE:
<223> OTHER INFORMATION: MdMLO11 Reverse Primer

<400> SEQUENCE: 10
aagcacgtga aagacggcta                                                  20

<210> SEQ ID NO 11
<211> LENGTH: 20
<212> TYPE: DNA
<213> ORGANISM: Artificial Sequence
<220> FEATURE:
<223> OTHER INFORMATION: MdMLO19 Forward Primer

<400> SEQUENCE: 11
cagagtggcg actgcactta                                                  20

<210> SEQ ID NO 12
<211> LENGTH: 20
<212> TYPE: DNA
<213> ORGANISM: Artificial Sequence
<220> FEATURE:
<223> OTHER INFORMATION: MdMLO19 Reverse PRimer

<400> SEQUENCE: 12
gggacatgga gtgcaaagga                                                  20

<210> SEQ ID NO 13
<211> LENGTH: 22
<212> TYPE: DNA
<213> ORGANISM: Artificial Sequence
<220> FEATURE:
<223> OTHER INFORMATION: MdMLO11 Forward Primer

<400> SEQUENCE: 13
gcacatcgca gcgaagaagc ac                                               22

<210> SEQ ID NO 14
<211> LENGTH: 25
<212> TYPE: DNA
<213> ORGANISM: Artificial Sequence
<220> FEATURE:
<223> OTHER INFORMATION: MdMLO11 Reverse Primer

<400> SEQUENCE: 14
agctttcagt gtcctgttcg gattg                                            25
```

```
<210> SEQ ID NO 15
<211> LENGTH: 24
<212> TYPE: DNA
<213> ORGANISM: Artificial Sequence
<220> FEATURE:
<223> OTHER INFORMATION: MdMLO19 Forward Primer

<400> SEQUENCE: 15
tgcacttgct ttctttgcat ggac                                              24

<210> SEQ ID NO 16
<211> LENGTH: 25
<212> TYPE: DNA
<213> ORGANISM: Artificial Sequence
<220> FEATURE:
<223> OTHER INFORMATION: MdMLO19 Reverse Primer

<400> SEQUENCE: 16
aacgacatct tccaacttct catgg                                             25

<210> SEQ ID NO 17
<211> LENGTH: 20
<212> TYPE: DNA
<213> ORGANISM: Cauliflower mosaic virus

<400> SEQUENCE: 17
cgcacaatcc cactatcctt                                                   20
```

PODOSPHAERA LEUCOTRICHA RESISTANCE PROVIDING GENES IN MALUS DOMESTICA

CROSS-REFERENCE TO RELATED APPLICATIONS

This application is the United States national phase of International Application No. PCT/EP2016/073783 filed Oct. 5, 2016, and claims priority to International Application No. PCT/EP2015/073135 filed Oct. 7, 2015, the disclosures of which are hereby incorporated in their entirety by reference.

The Sequence Listing associated with this application is filed in electronic format via EFS-Web and is hereby incorporated by reference into the specification in its entirety. The name of the text file containing the Sequence Listing is 1802895_ST25.txt. The size of the text file is 10,606 bytes, and the text file was created on Mar. 28, 2018.

The present invention relates to *Podosphaera leucotricha* resistance conferring genes, plants, plant parts and seeds comprising the present resistance providing genes and the use thereof for selecting *Podosphaera leucotricha* resistant plants.

Powdery mildew (PM) is a major fungal disease for thousands of plant species, including cultivated Rosaceae such as apple (*Malus domestica*), apricot (*Prunus armeniaca*), peach (*Prunus persica*), and strawberry (*Fragaria* x *ananassa*). Powdery mildew occurs in all major growing regions of Rosaceous crops, leading to severe losses.

Apple powdery mildew caused by the fungus *P. leucotricha*, is one of the most economically relevant diseases of apple, worldwide. The symptoms are white spots on young green tissues, particularly leaves in the first days after opening, whereas mature leaves show some resistance. Infected leaves crinkle, curl, and prematurely drop. Blossoms and fruits are not the primary targets PM fungi, but infections of these tissues are possible. Powdery mildew spores overwinter in buds and then in spring, with the reprise of vegetative growth, they start a new infection. PM of apple occurs in all apple-producing regions of the world. The disease causes economic damage by reducing tree vigor, flower bud production, and fruit quality. PM of apple produces symptoms on young shoots, leaves, blossoms, and fruit. In general, symptoms are most noticeable on the leaves and fruit.

*P. leucotricha* is an ascomycete fungus of the *Erysiphaceae* family. During the growing season, this obligate biotroph continuously produces asexual spores (conidia) on specialized short stalks called conidiophores and sexual spores (ascospores) in sac-like asci enclosed in fruiting bodies (ascocarps). Conidia are hyaline (clear, without color) and contain distinct fibrosin bodies, whereas each ascocarp (black) contains a single ascus with eight elliptical ascospores densely grouped together. The hyaline's fibrosin bodies are refractive inclusion bodies that exhibit varied shapes including rods and cones. Ascocarps do not play any known role in initiating new epidemics, as the ascospores fail to germinate readily. Conidia are wind-dispersed and do not require free moisture to germinate. If they land on susceptible tissue, they initiate infection and produce mycelium.

In commercial orchards, fungicides are almost always used to control mildew, as well as other apple diseases. However *P. leucotricha* has exhibited the ability to develop resistance to these fungicides when they are used repeatedly. Benzimidazoles was activity against *P. leucotricha*, but their utility in apple disease management is now limited, due to widespread resistance development in *Venturia inaequalis* (apple scab). Fungicides are usually applied at 7- to 10-day intervals from the tight-cluster stage until terminal shoot growth ends to ensure that the application coincides with rapid leaf development and the post-bloom period, and that the new growth do not remain unprotected for long. Furthermore, the intense application of fungicides has several drawbacks. First of all, the effects on the environment are well documented. Secondly, the costs of the chemicals and their applications can reach up to 20% of the total expenses for apple production in some areas. Thirdly, the development of resistant populations of the pathogen was already documented by Baudoin et al. (2008) and Dufour et al. (2011), strongly reducing the efficacy of chemical treatments. Therefore, there is increasing interest in the development of new alternative methods to control PM.

The generation of PM-resistant varieties is one of the best options to make sustainable apple cultivation a realistic possibility, preserving at the same time the incomes of the growers. The use of less susceptible apple cultivars may be the most effective means of preventing PM. Apple cultivars, including 'Jonafree', 'Prima' and 'Enterprise', demonstrate natural resistance to PM, but they are not widely cultivated. Cultivar selection is influenced more by commercial appeal, fruit qualities, marketability, and pollination characteristics than by disease resistance. Apple cultivars such as 'Golden Delicious', 'Idared' and 'Granny Smith', are widely grown, but are highly susceptible to PM and require chemical disease management.

The most common strategy to develop resistant plants is focused on the introgression of resistance genes (R-genes). R-genes encode proteins that recognize pathogen effectors and trigger defense response, mediated by a signaling network in which plant hormones play a major role (Pavan et al., 2010). Resistance is manifested as localized hypersensitive response at the site of infection (Robert-Seilaniantz et al., 2007; Bruce and Pickett, 2007; Bari and Jones, 2009). R-genes are scarcely durable, as mutations of pathogen effectors, allow to overcome resistance (Parlevliet et al., 1993). Furthermore, R-genes often originate from wild-relatives of the cultivated species, and thus interspecific crossability barriers could prevent their introgression. Moreover, in case of a successful cross, several undesirable traits are incorporated with the R-gene, making extensive back-crossing necessary, which is time-consuming in woody species like apple.

An alternative approach is based on the inactivation of susceptibility genes (S-genes), defined as genes whose loss-of-function results in recessively inherited resistance (Pavan et al., 2010). Some pathogens are able to suppress plant defense by activating plant proteins which function is the negative regulation of plant immunity system. The genes encoding these plant proteins are known as susceptibility genes (S-genes) and their knock-out release the suppression of plant defense and lead to resistance (Pavan et al., 2010). The disadvantage of S-genes is the pleiotropic phenotypes sometimes associated to their knock-out (Pavan et al. 2011). Mildew Locus O (MLO) genes are a typical example of PM S-genes.

Resistance due to the knock-out of an MLO gene (mlo resistance) was discovered in barley in 1992 (Jorgensen, 1992) and for a long time was considered as a unique form of resistance. However, further studies revealed that MLO genes are largely conserved across plant kingdom and their loss-of-function resulted in resistance in several species, such as *Arabidopsis* (Consonni et al., 2006), pea (Pavan et al., 2011), tomato (Bai et al., 2008) and pepper (Zheng et al., 2013). Not all MLO genes are S-genes and MLO family members are divided in seven clades (Acevedo-Garcia et al., 2014; Pessina et al., 2014). Only two clades contain S-genes: clade IV contains all monocots S-genes (Panstruga et al., 2005; Reinstädler et al., 2010) and clade V contains all dicots S-genes (Consonni et al., 2006; Bai et al., 2008; Feechan et al., 2008; Winterhagen et al., 2008). Not all the members of clades IV and V are S-genes.

Considering the economic impact of a *P. leucotricha* infection on apple production, there is a continuos need in the art for *P. leucotricha* resistance providing genes.

SUMMARY OF THE INVENTION

It is an object of the present invention, amongst other objects, to meet this need of the art.

According to the present invention, the above object, amongst other objects is met by providing impaired *P. leucotricha* resistance providing genes as outlined in the appended claims.

Specifically, the above object, amongst other objects, is met according to a first aspect of the present invention by providing *P. leucotricha* resistance conferring genes, wherein the amino acid sequence encoded by the resistance conferring gene is the primary amino acid sequence represented by SEQ ID No. 1, or a primary amino acid sequence with more than 70% identity, preferably more than 80% identity, more preferably more than 90% identity, and most preferably more than 95% identity with SEQ ID No. 1 under the condition that the present resistance conferring genes are impaired.

Sequence identity as used herein is defined as the number of identical consecutive aligned nucleotides, or amino acids, over the full length of the present sequences divided by the number of nucleotides, or amino acids, of the full length of the present sequences and multiplied by 100%. For example, a sequence with 80% identity to SEQ ID No. 1 comprises over the total length of 589 amino acids of SEQ ID No. 1, 471 or 472 identical aligned amino acids, i.e., 471 or 472/589*100%=80%.

An impaired resistance conferring gene according to the present invention is meant to indicate a gene providing a reduced, or even absent, susceptibility to *Podosphaera leucotricha* as indicated by powder-like spots on the leaves and stems.

Impaired resistance conferring genes according to the present invention are mutated genes. The mutation, or mutations, in the present genes can results/result in impairment by different mechanisms. For example, one or more mutations in protein encoding DNA sequences can result in mutated, truncated or non-functional proteins. One or more mutations in non-coding DNA sequences can cause alternative splicing, translation or protein trafficking. Alternatively, one or more mutations resulting in an altered transcriptional activity of a gene, which determines the amount of mRNA available for translation to protein, can result in a resistance due to a low level, or complete absence, of encoded proteins. Additionally, the impairment of the present genes may be caused after translation, i.e. at protein level.

Impaired is also indicated herein as encoding a non-functional gene or protein. Although the function of the present genes is not yet identified, a non-functional gene or protein can be readily determined by establishing *Podosphaera leucotricha* resistance (non-functional) or *Podosphaera leucotricha* susceptibility (functional) in a plant. A *Podosphaera leucotricha* resistance (non-functional) plant is indicated by comprising a gene which is mutated at the protein level as compared to the SEQ ID No. 1 or no or reduced levels are observed of mRNA comprising SEQ ID No. 2.

Functional and non-functional genes, or proteins, can also be determined using complementation experiments. For example, transforming a *Podosphaera leucotricha* resistant *Malus domestica* plant with a copy the present genes under the control a constitutive promoter will result in a *Podosphaera leucotricha* susceptible *Malus domestica* plant.

According to the present invention, the present *Podosphaera leucotricha* resistance conferring genes provide *Podosphaera leucotricha* resistance when impaired. Impaired according to the present invention can be indicated by the absence, or decrease of a protein identified herein by SEQ ID No. 1. In the art, many mechanisms are known resulting in the impairment of a gene either at the transcription, translation or protein level.

For example, impairment at the transcription level can be the result of one or more mutations in transcription regulation sequences, such as promoters, enhancers, initiation, termination or intron splicing sequences. These sequences are generally located 5' of, 3' of, or within the coding sequences represented by SEQ ID No. 2. Impairment can also be provided by a deletion of, rearrangement of or insertion in the present genes.

Impairment at the translation level can be provided by a premature stop-codons or other RNA to protein controlling mechanisms or posttranslational modifications influencing, for example, protein folding or cellular trafficking.

Impairment at the protein level can be provided by truncated, misfolded or disturbed protein-protein interactions.

Independent of the underlying mechanism, impairment according to the present invention is indicated by a decrease, or absence, a functional protein according to SEQ ID No. 1.

Considering the above, according to an embodiment of the first aspect of the present invention, impairment according to the present invention comprises one or more mutations in the present genes resulting in the absence of a protein expression product with a primary amino acid sequence represented by SEQ ID No. 1 or an mRNA comprising SEQ ID No. 2.

According to another embodiment of this first aspect of the present invention, the present impairment comprises one or more mutations in the present genes resulting in a non-functional protein expression product.

According to still another embodiment of this first aspect of the present invention, the present impairment comprises a reduced transcription level resulting in a reduced level of an mRNA comprising SEQ ID No. 2.

According to yet another embodiment of this first aspect of the present invention, the present impairment comprises a reduced translation level of an mRNA comprising SEQ ID No. 2.

According to an especially preferred embodiment of the invention, the present *Podosphaera leucotricha* resistance conferring gene is derived from *Malus domestica*.

According to a second aspect, the present invention relates to *Malus domestica* plants comprising in their genome an impaired *Podosphaera leucotricha* resistance conferring gene as described above wherein the impairment provides *Podosphaera leucotricha* resistance.

According to a preferred embodiment of this second aspect of the present invention, the present *Malus domestica* plants show an expression, or transcription, of the present *Podosphaera leucotricha* resistance conferring genes being reduced by at least 10% as compared to a *Malus domestica* plant susceptible to *Podosphaera leucotricha*, preferably wherein the expression, or transcription is reduced by at least 20% as compared to a *Malus domestica* plant susceptible to *Podosphaera leucotricha*, preferably at least 30%, more preferably at least 50%, even more preferably at least 70%, and most preferably at least 80% such as 25%, 35%, 40%, 45%, 55%, 60%, 65% or 75%.

According to another preferred embodiment of this second aspect of the present invention, the present *Malus domestica* plants display an absent expression, or transcription of the present *Podosphaera leucotricha* resistance conferring genes.

According to an especially preferred embodiment of this second aspect of the present invention, the present *Malus domestica* plants comprise in their genome an impaired *Podosphaera leucotricha* resistance conferring gene encoding a protein with the primary amino acid sequence of SEQ ID No. 1, or a primary amino acid sequence with more than 70% identity, preferably more than 80% identity, more preferably more than 90% identity, and most preferably more than 95% identity with SEQ ID No. 1; Formulated differently, the present invention relates according to an especially preferred embodiment to *Malus domestica* plants comprising an impaired Mdmlo19 gene or comprising an impaired MdMLO19 gene.

According to a third aspect, the present invention relates to seeds, plant parts or propagation material of the present *Podosphaera leucotricha* resistant plants comprising in their genome the present an impaired *Podosphaera leucotricha* resistance conferring gene providing *Podosphaera leucotricha* resistance.

According to a fourth aspect, the present invention relates to isolated nucleotide sequence represented by SEQ ID No. 2, or nucleotide sequences with more than 70% identity, preferably more than 80% identity, more preferably more than 90% identity, and most preferably more than 95% identity therewith.

According to a fifth aspect, the present invention relates to isolated amino acid sequences represented by SEQ ID No. 1, or amino acid sequences with more than 70% identity, preferably more than 80% identity, more preferably more than 90% identity, and most preferably more than 95% identity therewith.

According to a sixth aspect, the present invention relates to the use of the present *Podosphaera leucotricha* resistance conferring gene, the present isolated nucleotide sequence or the present isolated amino acid sequence for selecting an *Podosphaera leucotricha* resistant *Malus domestica* plants using, for example, the present sequence for developing molecular markers.

BRIEF DESCRIPTION OF THE DRAWINGS

The present invention will be further detailed in the example below. In the example, reference is made to figures wherein.

DESCRIPTION OF THE INVENTION

EXAMPLE

Figure 1:
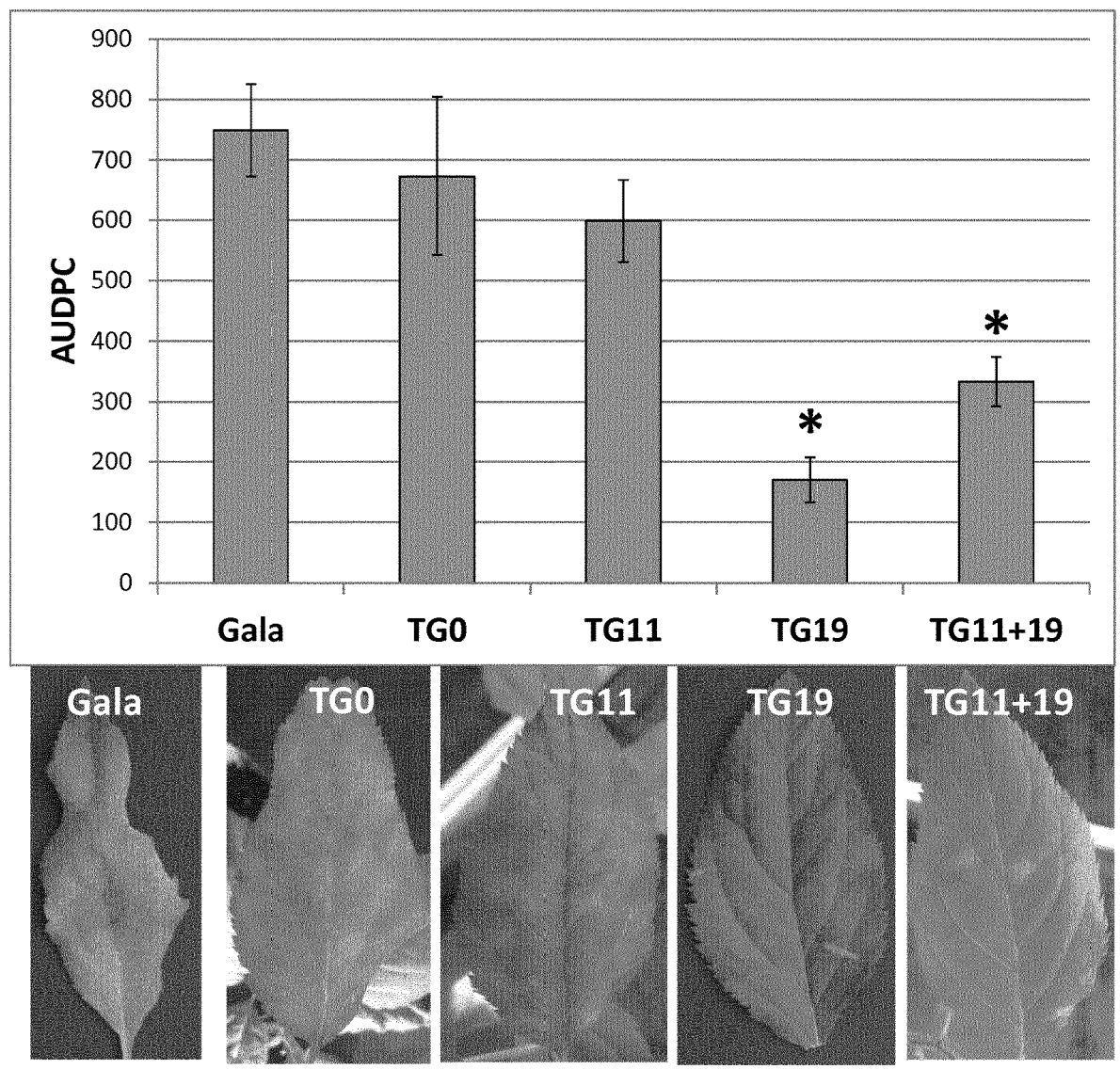
FIG. 1: shows the area under disease progress curve (AUDPC) of four apple mlo lines and of the control 'Gala', inoculated with *Podosphaera leucotricha*. Average AUDPC was calculated from 15 to 24 biological replicates considered in four experiments. Error bars show the standard errors of the mean. Statistically significant differences in the comparisons with 'Gala', according to Tukey and Games-Howell post-hoc tests (P=0.05) are indicated with asterisks.

*Malus* is a genus composed of numerous widely dispersed and diverse taxa, yet nearly all of the world's commercial apple production is concentrated within a single species, *Malus domestica*, which is native to Asia. *M. domestica* is highly susceptible to PM, with relatively minor differences among cultivars and selections.

The control of PM in commercial orchards generally requires the significant use of fungicides, which has an economical impact for apple producers. Numerous organic and inorganic fungicides are used to control *P. leucotricha*. However *P. leucotricha* has exhibited hability to develop resistance to these materials when they are used repeatedly, and also these synthetic products are not environmentally friendly.

To improve the resistance of apple to this disease, breeders began to introduce genetic resistance from wild *Malus* spp. into *M. domestica*, resulting in many *Malus* hybrids (such as White Angel).

Three binary RNAi vectors were developed to silence 2 MLO genes. Inoculation of transgenic "Gala" mutated for the MLO genes, showed that silencing of the MdMLO19 gene increase the resistance of *M. domestica* to *P. leucotricha*. A decrease up to 75% of the susceptibility to this disease was observed in the mutated "Gala" line with a level of silencing of MLO around 90%.

Screening the resequencing data of 63 apple cultivars, we discovered a natural loss-of-function mutation in MdMLO19. No similar mutations were found in the other four MLO genes considered (MdMLO5, 7, 11 and 18). When this mutation is present at both alleles, the apple cultivar is resistant.

Materials and Methods

Constructs for MdMLO11 and MdMLO19 Knock-Down in Apple

Gene fragments for RNAi were amplified from MdMLO11 and MdMLO19 (accession numbers in Table 1) with primers listed in Table 2 and cloned in gateway pENTR/SD-TOPO (Thermo Fisher Scientific, Waltham, USA). In addition, a chimeric construct was developed joining RNAi fragments supposed to silence MdMLO11 and MdMLO19 simultaneously (Abbott et al., 2002). For this purpose, a restriction site for EcoRI was added at the 3' end of the MdMLO11 RNAi fragment and at the 5' end of the MdMLO19 one. Both fragments were restricted with EcoR1 and joined with a T4 DNA ligase (New England Biolabs, Ipswich, USA). The resulting construct was cloned into the pENTR vector. After sequencing, all fragments were cloned into the destination vector pHELLSGATE 12 (Thermo Fisher Scientific, Waltham, USA). The final constructs were verified by sequencing, and inserted into A. tumefaciens strain AGL0 through electroporation. A. tumefaciens transformed cells were tested by PCR for the presence of the constructs, using specific primers designed to anneal on vector and MLO sequences.

Skoog medium with vitamins, 30 g/L of sucrose, 0.7 mg/L of BAP, 96 mg/L of FeEDDHA, pH 5.8. To promote rooting, plants were transferred on a medium containing IBA to promote rooting. Once roots were formed, plants were progressively acclimated to greenhouse conditions (25° C., 16-h-light/8-h-dark cycle, relative humidity 70±5%) in 125 ml pots covered with plastic bags and containing wet autoclaved turf ("Terriccio Vegetal Radic"—Tercomposti Spa, Brescia, Italy). Every 5-7 days for three weeks, air humidity was reduced to promote the formation of the foliar cuticle. Plastic bags were then removed and plants were transferred to 1 L pots. The control (untransformed in vitro grown 'Gala') was acclimated as described above.

P. leucotricha Inoculation and Disease Severity Assessment in Apple

To produce a PM inoculum, local strains of *Podosphaera leucotricha* were isolated from infected leaves of an orchard located in the Trentino province (Italy). The fungus was

TABLE 1

Primers for qPCR

| Name | Accession number | Forward ('5-'3) | Reverse ('5-'3) |
|---|---|---|---|
| EF1 | MD09G014760[a] | TACTGGAACATCACAGGCTGAC (SEQ ID NO: 3) | TGGACCTCTCAATCATGTTGTC (SEQ ID NO: 4) |
| Ubiquitin | MD05G001920[a] | CATCCCCCCAGACCAGCAGA (SEQ ID NO: 5) | ACCACGGAGACGAAGCACCAA (SEQ ID NO: 6) |
| Md8283 | MDP0000375455[b] | CTCGTCGTCTTGTTCCCTGA (SEQ ID NO: 7) | GCCTAAGGACAGGTGGTCTATG (SEQ ID NO: 8) |
| MdMLO11 | MDP0000239643[b] | ATCGAAGGCTGTTGGAGCAA (SEQ ID NO: 9) | AAGCACGTGAAAGACGGCTA (SEQ ID NO: 10) |
| MdMLO19 | MDP0000168714[b] | CAGAGTGGCGACTGCACTTA (SEQ ID NO: 11) | GGGACATGGAGTGCAAAGGA (SEQ ID NO: 12) |

[a] Available at http://bioinformatics.psb.ugent.be/plaza
[b] Available at http://www.rosaceae.org/gb/gbrowse/malus_x_domestica/

TABLE 2

Primers for RNAi

| Gene | Accession number[a] | Primer Forward | Primer Reverse | Amplicon Lenght |
|---|---|---|---|---|
| MdMLO11 | MDP0000239643 | GCACATCGCAGCGAAGAAGCAC (SEQ ID NO: 13) | AGCTTTCAGTGTCCTGTTCGGATTG (SEQ ID NO: 14) | 134 bp |
| MdMLO19 | MDP0000168714 | TGCACTTGCTTTCTTTGCATGGAC (SEQ ID NO: 15) | AACGACATCTTCCAACTTCTCATGG (SEQ ID NO: 16) | 115 bp |

[a] Available at http://www.rosaceae.org/gb/gbrowse/malus_x_domestica/.

Development of RNAi Apple Plantlets

The RNAi-constructs were transferred into apple as described by Joshi et al. (2011). Explants from the top four leaves of 4-week-old in vitro propagated shoots of the cultivar Gala were kept on a medium with kanamycin (Joshi et al., 2011), and grown in a growth chamber with 16-h-light/8-h-dark cycle at 24° C. To certify the presence of the constructs with PCR, genomic DNA from regenerated plantlets was extracted with the Illustra Nucleon Phytopure kit (GE Healthcare). The forward primer annealed on the CaMV 35S promoter (5'-CGCACAATCCCACTATCCTT-3') (SEQ ID NO: 17) and the reverse primers were specific for the RNAi fragments (Table 2). PCR was performed with GoTaq® Green Master Mix (Promega, Fitchburg, USA). Plants positive for the construct were moved to Shoot Propagation Medium (SPM): 4.4 g/L of Murashige and maintained by serial inoculations on *M. domestica* seedlings under greenhouse conditions. Plants were dry-inoculated by brushing the adaxial epidermis with leaves of infected seedlings. To promote the fungal penetration, plants were incubated in greenhouse at 25° C. with a relative humidity of 100% for 6 h. The plants were then maintained at 25° C. and 80±10% relative humidity until the end of the evaluation.

Four inoculation experiments were carried out in different periods of the year. In each test, three to eight biological replicates of each transgenic line were considered. Lines were tested in at least three out of four experiments and the total number of replicates varied between 15 and 24. Disease severity was visually assessed on all inoculated leaves 7, 14 and 21 dpi. Disease severity was expressed as the percentage (intervals of 5%) of adaxial leaf area covered by the PM mycelium, and a single plant mean value was calculated. Reduction of disease severity in transformed plants was expressed as [(severity in controls−severity in transgenics)/severity in controls]×100%. To consider all time points together, the area under the disease progress curve (AUDPC), summarizing disease intensity over time (Campbell and Madden, 1990; Madden et al., 2007), was calculated. The number of *P. leucotricha* conidia present on infected leaves was assessed as in Angeli et al. (2012) with slight modifications: three leaves were collected from each replicate at 21 dpi and four disks of 0.8 cm diameter for each leaf were cut for a total of 12 per replicate. Leaf disks were transferred to 50 ml tubes containing 5 ml distilled water with 0.01% Tween 20 (Sigma-Aldrich, Saint Louis, USA). Tubes were vortexed for one minute and the concentration of conidia per ml was determined by counting with a hemocytometer under a light microscope. The amount of conidia was expressed as number per square centimeter ($cm^2$) of leaf.

Histological Analysis of Inoculated Apple Leaves

Two inoculated leaves for each replicate were collected at 3, 10 and 21 days post inoculation for bright field microscopy observations. To visualize fungal hyphae, leaves were cleared in ethanol:acetic acid (3:1 v/v) until chlorophyll removal (approximately 48 hours). Samples were stained for 15 minutes with 250 μg/ml trypan blue in lactic acid, glycerol, and water (1:1:1). After rinsing and mounting as in Vogel and Somerville (2000), hyphae were visualized under bright field illumination of a Leica LMD7000 microscope (Wetzlar, Germany).

Leaves considered for scansion electron microscopy (Hitachi S-2300, Tokyo, Japan) were fixed in Sorensen phospate buffer 0.1 M, pH 7, 3% gluteraldehyde. After 24 hours, leaves were washed in Sorensen buffer without gluteraldehyde for two hours under mild agitation (80-100 rpm). Afterwards, samples were progressively dehydrated with four ethanol washings at concentrations from 40 to 100%, dried and kept in falcon tubes until observation. Fragment of leaves were metallized with gold before observation. Images were processed with ImageJ software (http://imagej.nih.gov/ij/).

For the detection of papillae, leaves were cleared in ethanol:acetic acid (3:1, v/v) until chlorophyll removal, and equilibrated overnight in a solution of lactic acid, glycerol and water (1:1:1). Papillae were visualized using the LMD filter (BP filter 380-420 nm excitation, 415 dichroic mirror, and BP 445-485 nm emission) of a Leica LMD6500 microscope (Leica Microsystem, Wetzlar, Germany).

Gene Expression Analysis

To identify lines showing silencing effects, a first gene expression study used in vitro grown transgenic plants replicated three times. In the second study concerning acclimated transgenic plants, leaf samples were collected immediately before PM inoculation, at 24 hpi and at 10 dpi. For each line at each time point, leaf samples were collected from five different plants. Samples were frozen in liquid nitrogen and stored at 80° C. Total RNA was extracted with the Spectrum™ Plant Total RNA kit (Sigma-Aldrich), treated with the DNAse I (Sigma-Aldrich) and reverse transcribed using the SuperScript III reverse transcriptase (Invitrogen, Life Technologies, Waltham, USA). The qPCR analyses were run according to SsoAdvanced Universal SYBR Green Supermix, (Bio-Rad, Hercules, USA) in a 15-μl reaction volume, using a CFX96 Touch™ Real-Time PCR detection system (Bio-Rad, Hercules, USA), and the CFX Manager software. Samples were run in two technical replicates according the following thermal cycling parameters: 95° C. 3 min, 95° C. 10 sec, 55° C. 30 sec (repeated 40 times), 95° C. 10 sec. For the analysis of MdMLO19, the primer pairs considered in previous work were used (Table 1; Pessina et al., 2014). For MdMLO11 and for the expression of 17 genes involved in the interaction between apple and *P. leucotricha*, new primer pairs were designed with the NCBI Primer Designing Tool (http://www.ncbi.nlm.nih.gov/tools/primer-blast/) (Table 1). Serial dilutions of cDNA (1/10, 1/100, 1/1000 and 1/10000) allowed to calculate the efficiency of the primer pairs; the expected sizes of the products were confirmed using agarose gel electrophoresis. Presence of a specific final dissociation curve was determined after every qPCR run, with progressive increments of temperature from 65° C. to 95° C. (0.5° C. each step, 5 sec). The reference genes considered were elongation factor 1, ubiquitin and 8283 (Table 1). All of them are known to be stable reference genes for apple (Botton et al., 2011; Pessina et al., 2014). The analysis with the software geNorm (medgen.ugent.be/~jvdesomp/genorm) resulted in M-values lower than 1 for all three reference genes, in conditions where M-values lower than 1.5 are considered adequate (Ling and Salvaterra, 2011). The threshold cycles (Ct) were converted to relative expression levels as in Hellemans et al. (2007), using as input the average Ct of the two technical replicates. As reference Ct, the average Ct of wild-type 'Gala' at 0 hpi was adopted.

Statistics

Disease Severity

Severity data were analysed by the statistical package SPSS (IBM, Armonk, USA). For both apple and *A. thaliana*, severity data of leaves from the same plant were averaged before further analyses. Apple severity data of the eight younger leaves of a plant were considered, while *A. thaliana* data were from all leaves. Before any analysis, data were shown to be normally distributed (Kolmogorov-Smirnov and Shapiro-Wilk tests $P > 0.05$) and to have homogeneous variances (Levene's test, $P > 0.05$). One-way ANOVA with Tukey's post-hoc test was adopted to detect significant differences ($P < 0.05$) at each time point. Data were transformed according to $y = \arcsin(x)$, in order to meet the pre-requisites of ANOVA. In case of non-homogeneous variances, the Games-Howell's post-hoc test was applied. Prior to pooling data from independent experiments, the effect of single experiments was tested: no significant effect of the experiments emerged. Pooled data were analysed independently for time points 14 and 21 dpi. AUDPC data were treated as described above for severity data. Number of conidia data was analysed with one-way ANOVA, applying the Tukey post-hoc test ($P < 0.05$).

qPCR Data Analyses

For the evaluation of gene expression, relative expression values were transformed in logarithmic scale according to $Y = \ln(x)$ (Pessina et al., 2014) to meet normal distributions and homogeneities of variances, as assessed respectively with the test of Shapiro-Wilk ($P \leq 0.05$) and Levene ($P \leq 0.05$). Pairwise comparison of homoscedastic data was carried out with Tukey's test ($P < 0.05$), whereas non-homoscedastic data were analysed with Games-Howell test ($P < 0.05$), using the statistical package SPSS (IBM). To detect significant differences in expression, one-way ANOVA with Tukey post-hoc test ($P < 0.05$) was applied to data from samples collected at 0 hpi. Defense gene expression analysis, was tested with the Fisher post-hoc test.

Correlations

The two-tailed Pearson's correlation test was adopted to investigate the correlations between AUDPC and relative expression of MLO genes at 10 dpi, and between degree of severity and number of conidia, both at 21 dpi. All data have been transformed following y=arcsin(x) to achieve a normal distribution.

Metabolites

The data from the phenolic metabolites were subjected to one-way ANOVA with Fisher post-hoc test. In case of non-homoscedastic data, the Games-Howell post-hoc test was applied, and the Kruskall-Wallis non-parametric test for data not normally distributed.

Results

Development of RNAi Apple Plantlets

Three RNAi constructs were generated, two aimed at knocking-down MdMLO11 and MdMLO19 individually (i=KD-MdMLO11, ii=KD-MdMLO19), the third aimed at the simultaneous knock-down of MdMLO11 and MdMLO19 (iii=KD-MdMLO11+19). Eighty regenerated lines were obtained of which 48 did carry the RNAi insert as described in materials and methods (Table 3). The 48 transgenic lines were tested by qPCR to evaluate the level of MLO genes expression, but a significant knock-down was observed only in three of them (Table 3). In these three lines, off-target knock-downs were not detected for the other two clade V genes of apple (MdMLO5 and 7). The three Knock-down lines, named TG11 (Transgenic Gala MdMLO11), TG19 and TG11+19, were acclimated to greenhouse conditions, as well as the control wild-type 'Gala' and TG0, a line carrying the RNAi construct for MdMLO19 but not showing significant MLO genes knock-down. TG0, TG11, TG19 and TG11+19 will be indicated as transgenic lines, but only TG11, TG19 and TG11+19 as mlo lines.

The survival rate of plants to the acclimation procedure was above 90%. Under greenhouse conditions the mlo lines showed a normal growth compared to 'Gala' under greenhouse conditions.

TABLE 3 summary of gene transfer results

| Gene transfer | Knocked-down gene | Regenerated lines | Confirmed transgenic | Selected lines |
|---|---|---|---|---|
| i | MdMLO11 | 39 | 23 | TG11 |
| ii | MdMLO19 | 33 | 19 | TG0, TG19 |
| iii | MdMLO11 + MdMLO19 | 8 | 5 | TG11 + 19 |

Reduced Susceptibility to *P. leucotricha* of RNAi Apple Plants

The four transgenic lines and the control were tested for their susceptibility to PM in four independent experiments. TG0, the line not manifesting any MLO genes knock-down, showed a level of susceptibility to *P. leucotricha* comparable to that of the control; the same was noted for TG11, whereas TG11+19 and TG19 had an evident reduction of disease severity (FIG. 1). Although leaves of TG11+19 and TG19 plants were partially infected (FIG. 1), the extension of the adaxial leaf area covered in spores was significantly reduced compared to the control (FIG. 1). Table 4 summarizes the results on disease severity reduction.

Figure 2:
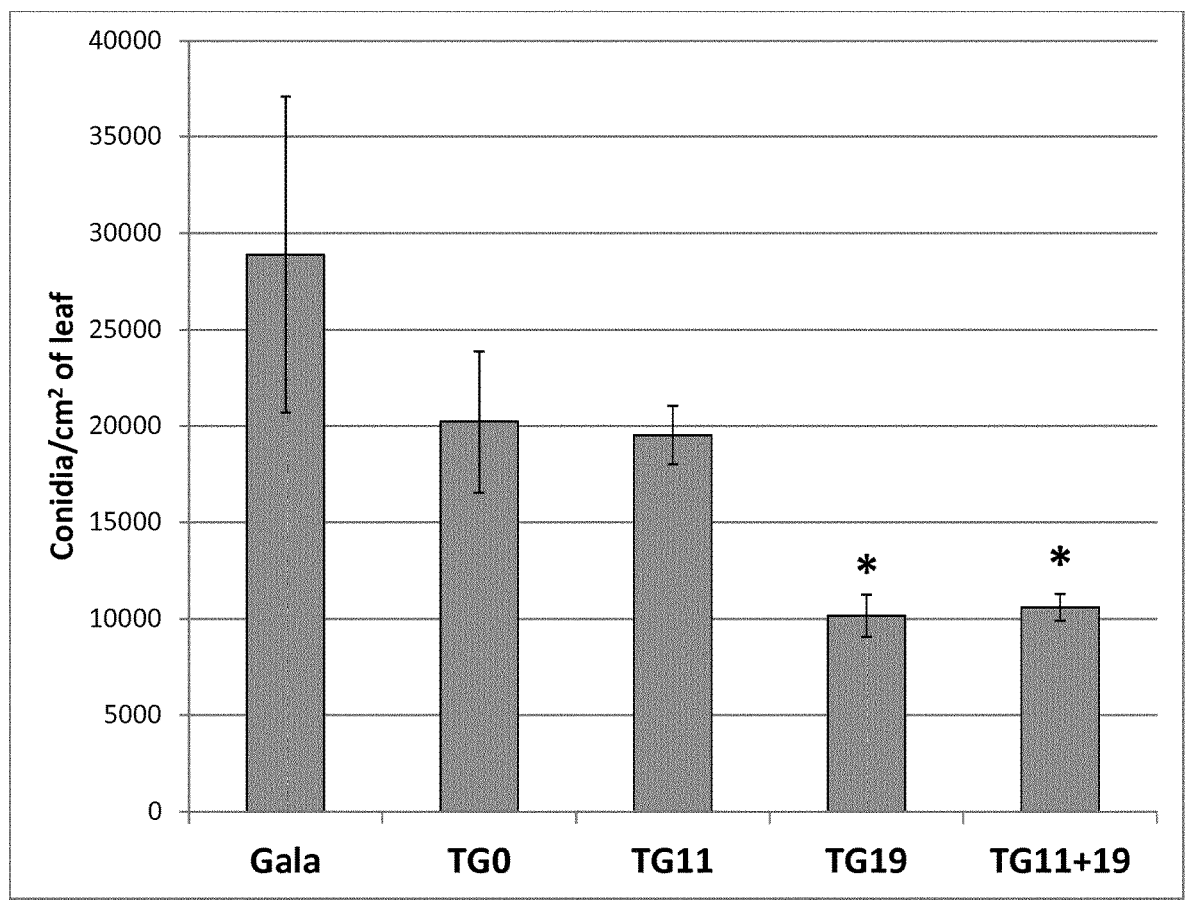
FIG. 2: shows the number of conidia per cm$^2$ leaf surface of 'Gala' and mlo lines TG0, TG11, TG19 and TG11+19 inoculated with *P. leucotricha* at 21 dpi. Bars indicate the average number of conidia, measured in two experiments. Error bars show standard errors of the mean. Asterisks indicate statistically significant differences compared to 'Gala' according to Tukey post-hoc test (P=0.01).

All the transgenic lines had a reduction in the number of conidia present on leaves (FIG. 2), but the decrease was statistically significant (P<0.05) only for TG11+19 and TG19. This compares well with the disease severity assessment presented in FIG. 1: compared to 'Gala', TG11+19 showed a 63.3% reduction in the number of conidia, and TG19 of 64.8%. A significant (P=0.01) but moderate positive correlation (Pearson coefficient of 0.525) was found between disease severity at 21 dpi and conidia count at 21 dpi.

Figure 3:
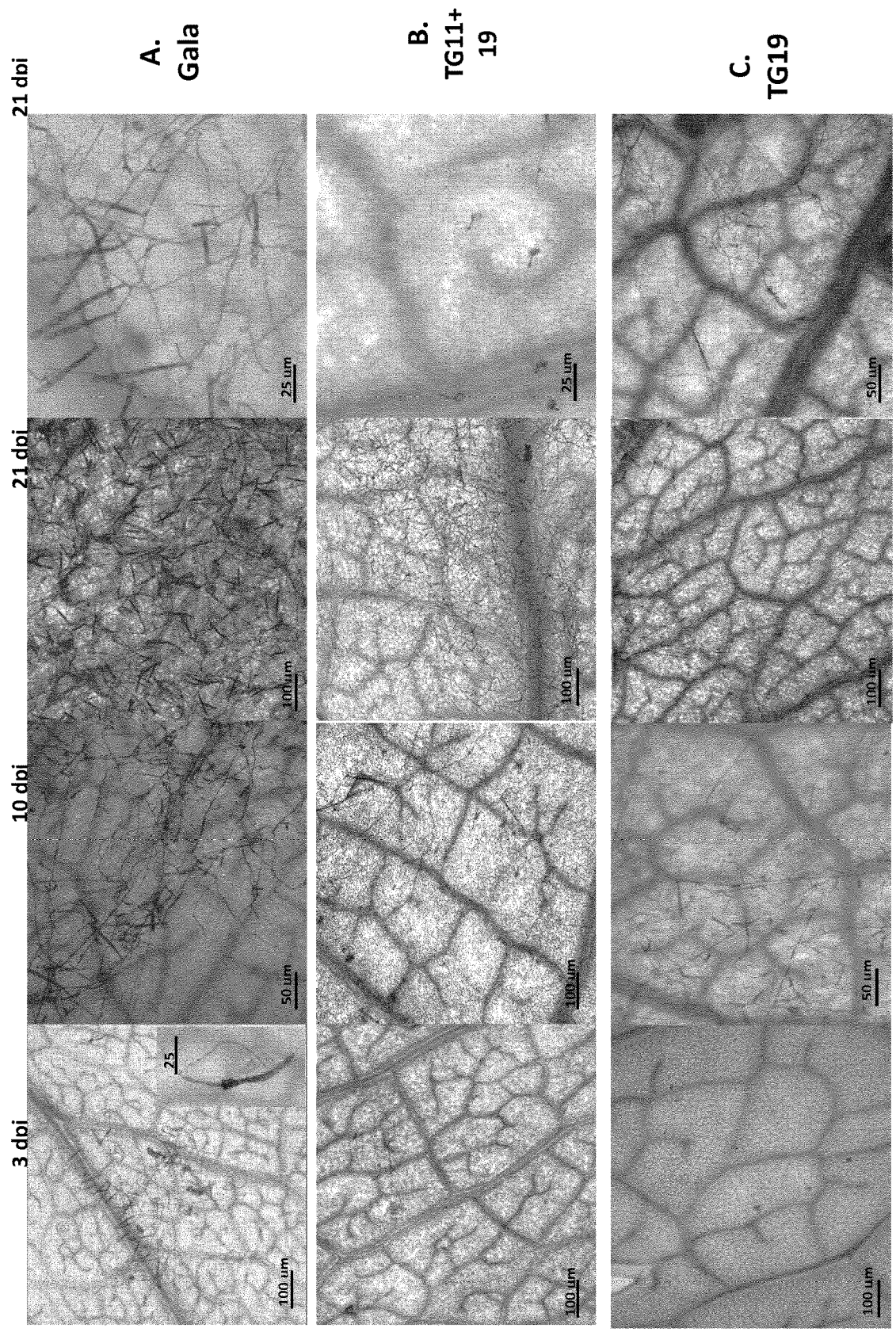
FIG. 3: shows bright field microscopy images of infected leaves of 'Gala' and lines TG11+19 and TG19 taken at 3, 10, and 21 dpi. For Gala at 3 dpi, at higher magnification the germination of a *P. leucotricha* spore is shown.
Figure 4:
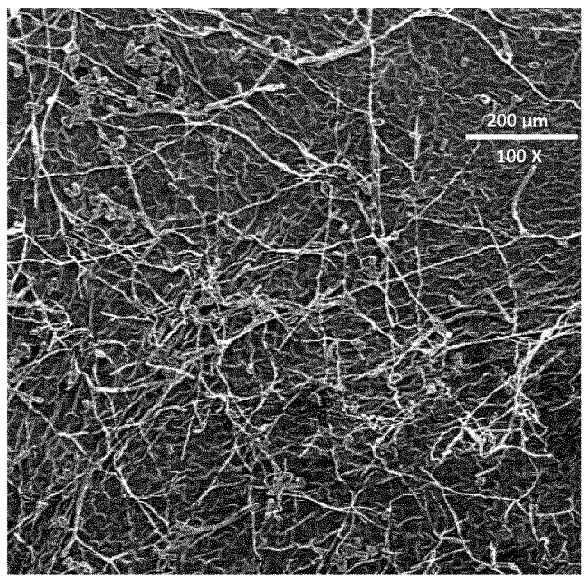
FIG. 4: shows SEM microscopy images of infected leaves of 'Gala', the susceptible line TG0 and the resistant line TG11+19. Pictures were taken at 21 dpi.
Figure 4:
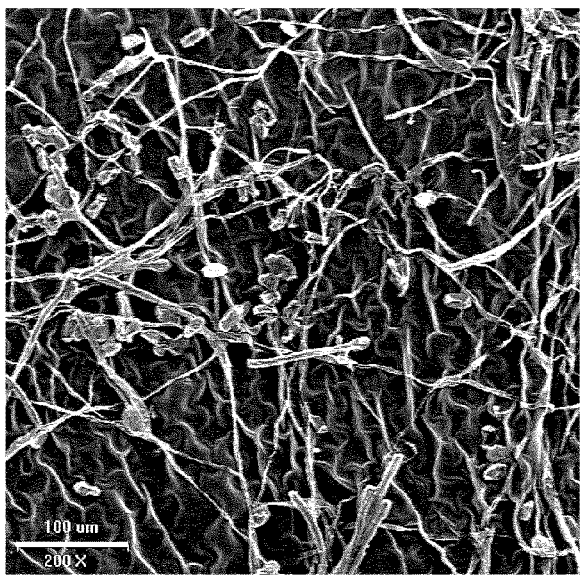
Figure 4:
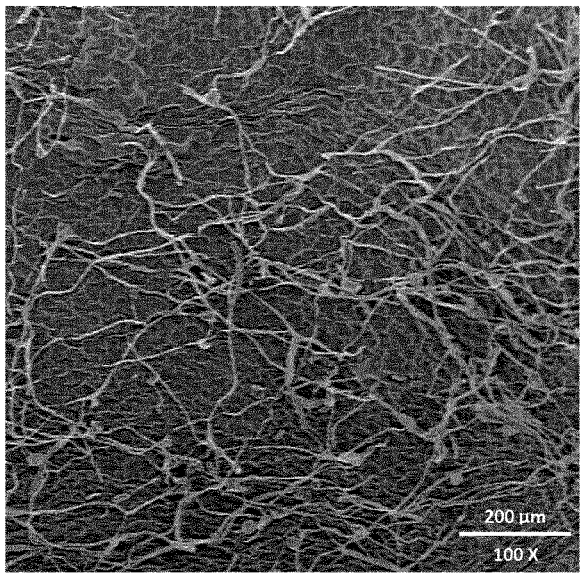
Figure 4:
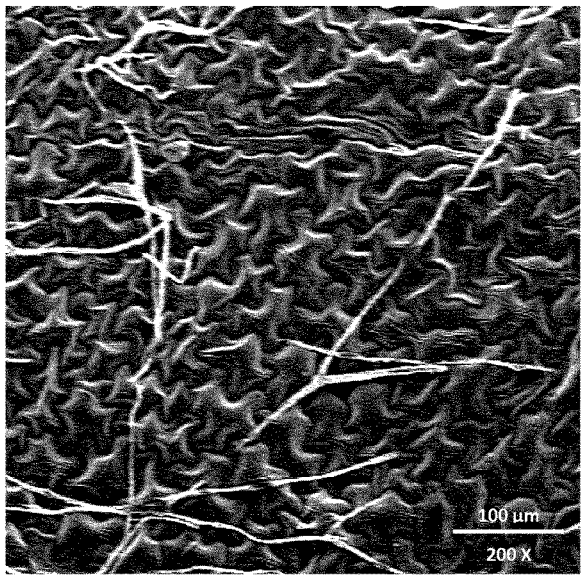
Figure 5:
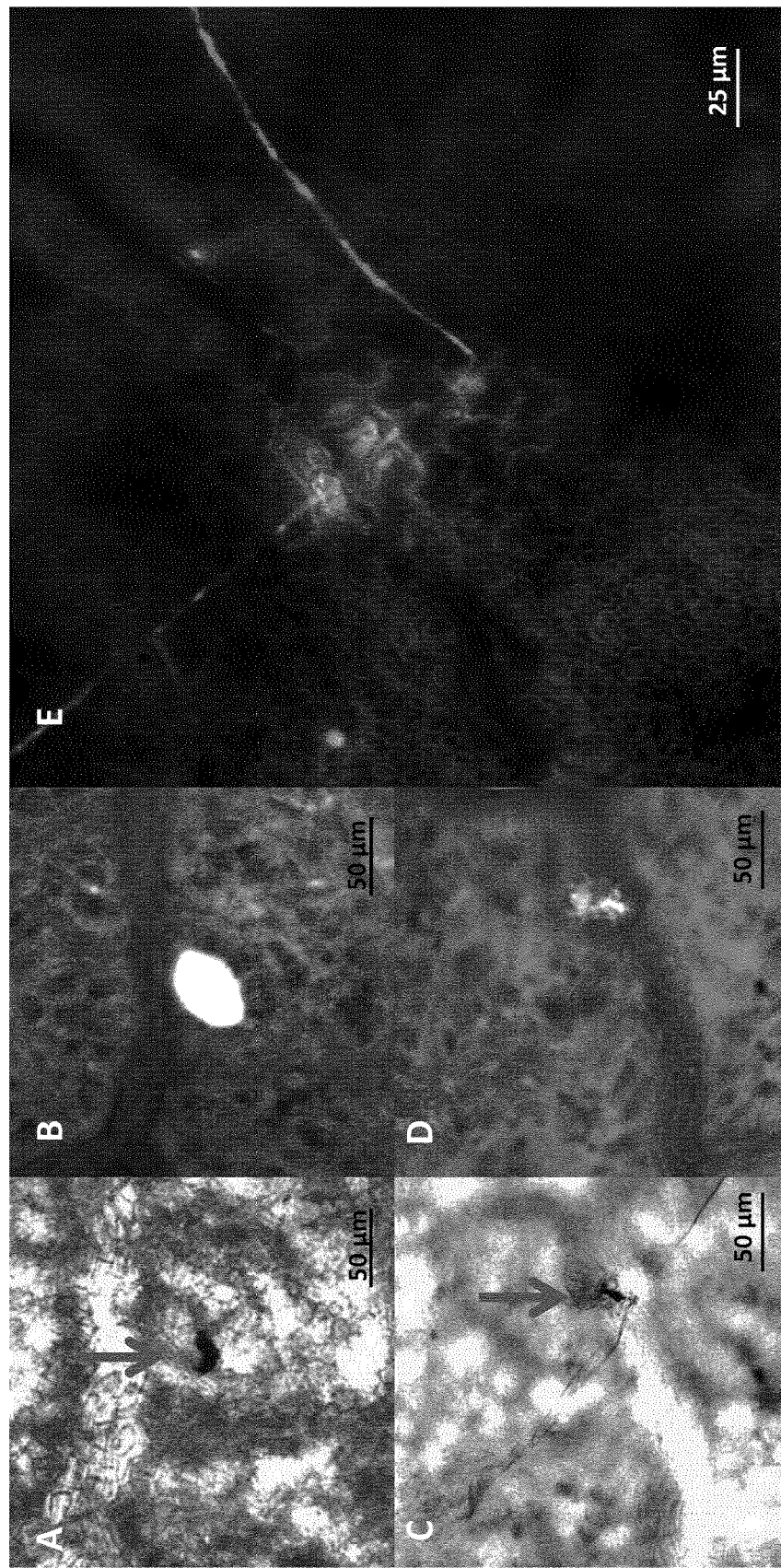
FIG. 5: shows formation at 3 dpi of papillae in infected leaves of 'Gala' (A, B) and in resistant lines TG11+19 (C, D) and TG19 (E). Images on the left were taken with a bright field microscope, those on the right with fluorescence microscope. For line TG19 only the image taken with the fluorescent microscope is shown.

Lines TG11+19 and TG19, together with 'Gala', were further analysed by bright field microscopy and scansion electron microscopy (SEM), to follow the development of *P. leucotricha* infection. In 'Gala', a well-developed leaf infection was observed already at 3 dpi (FIG. 3A), at the time when fungal development was still limited in TG11+19 and TG19 (FIGS. 3B and 3C). At 10 dpi, conidiophores were observed on leaves of all lines considered, but their number was higher in 'Gala' (FIG. 3). At 21 dpi, 'Gala' leaves were completely covered by spores and a large number of conidiophores were visible (FIG. 3A). The leaf surface of TG11+19 and TG19 was partially colonized by sporulating mycelium, but isolated spores unable to develop were also observed, as well as a smaller number of conidiophores compared to the situation noted for 'Gala' (FIGS. 3B and 3C). The SEM images showed reduced growth of the mycelium on TG11+19 compared to TG0 and 'Gala' (FIG. 4).

Figure 6:
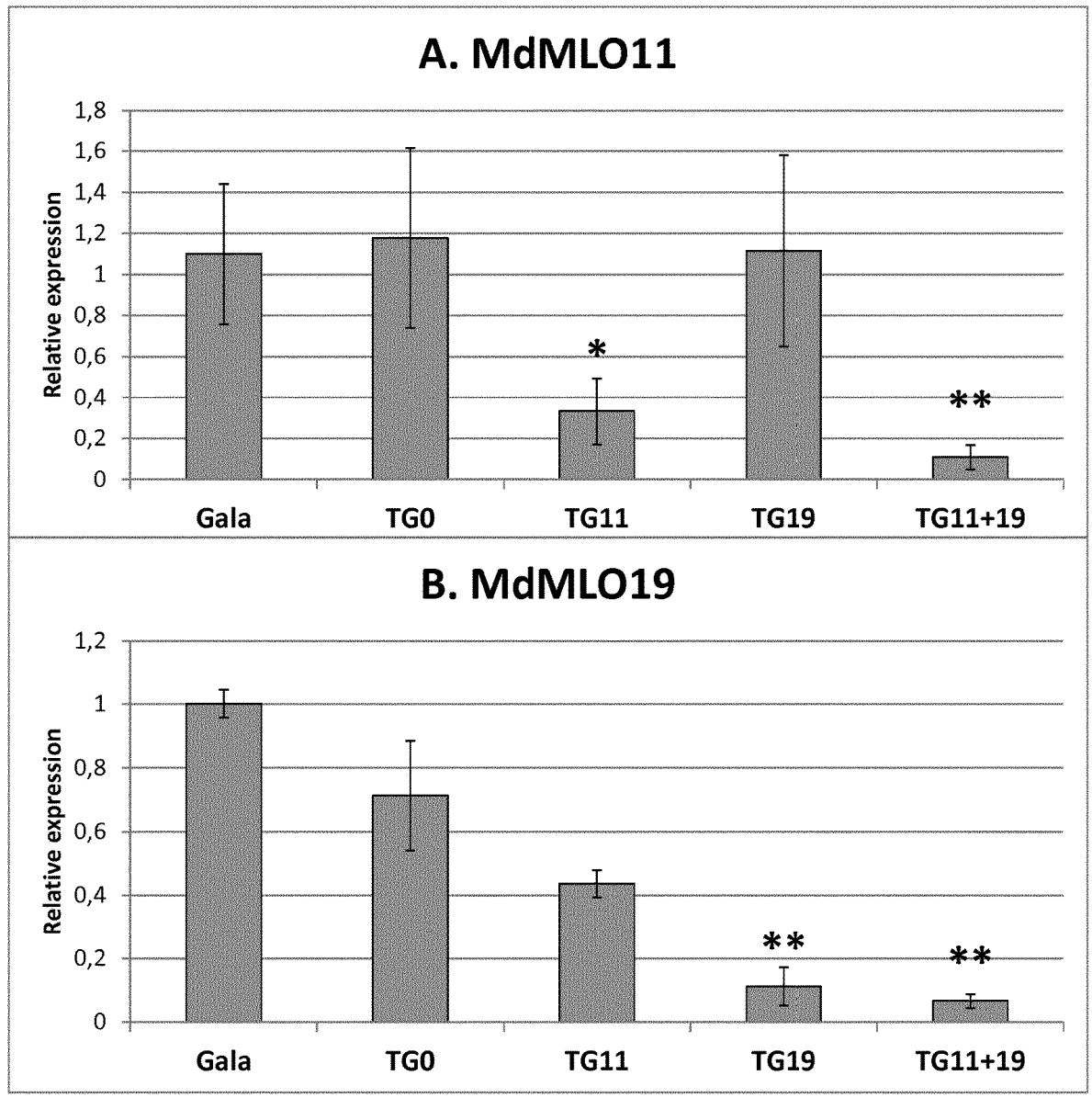
FIG. 6: shows expression of two apple MLO genes in five mlo lines in absence of *P. leucotricha* infection. Each bar represents the line average relative expression, evaluated from three to five plants. Error bars show the standard errors of the mean. Asterisks indicate significant differences in the comparison of mlo lines with 'Gala', based on Tukey or Games-Howell post-hoc tests (P=0.05).

The formation of papilla was observed at 3 dpi in all the lines, both resistant and susceptible (FIG. 6). Compared to TG11+19 and TG19, the papillae of 'Gala' (FIG. 6A,B) were smaller, the shape more defined and the fluorescence emitted was more intense (FIG. 6C,D,E).

TABLE 4

Powdery mildew disease severity reduction (%) in lines transformed with MLO RNAi constructs.

| | | Number of replicates | Disease severity reduction[#] | | |
|---|---|---|---|---|---|
| | Silenced genes | | 14 dpi | 21 dpi | Average |
| TG0 | / | 17 | 24.1 | 24.8 | 24.5 |
| TG11 + 19 | MdMLO11 and 19 | 23 | 60.0* | 52.6* | 56.3 |
| TG19 | MdMLO19 | 15 | 72.7* | 78.1* | 75.4 |
| TG11 | MdMLO11 | 16 | 38.0 | −3.2° | 17.4 |

*Statistically significant difference compared to the control, according to the Tukey post-hoc test (P = 0.05).
[#]Gala was used as control (19 plants) and assumed to have 0% of disease reduction.
°Line TG11 showed a higher level of infection compared to Gala at 21 dpi.

Expression of MLO Genes in mlo Apple Lines

Gene expression analysis of mlo lines previously selected was repeated in greenhouse acclimated plants. MdMLO11 was significantly less expressed in TG11+19 (P=0.01) and TG11 (P=0.05) (FIG. 6A), whereas the expression of MdMLO19 was reduced in TG11+19 (P=0.01) and TG19 (P=0.01) (FIG. 6B). MdMLO5 and MdMLO7, the two other apple members of Clade V, were also tested but no significant reduction was observed in any transgenic line, a finding supporting the absence of off-target silencing (data not shown).

Correlation between the expression of MdMLO19 and AUDPC—a measure of disease severity—was statistically significant (P=0.05), although moderate (Pearson coefficient=0.515). On the contrary, no significant correlation was found between AUDPC and the expression of MdMLO11.

Discussion

Natural and artificial loss-of-function mutations of MLO S-genes reduce susceptibility to PM pathogens, as described in barley (Büschges et al., 1997), *A. thaliana* (Consonni et al., 2006), pea (Pavan et al., 2011), tomato (Bai et al., 2008) and pepper (Zheng et al., 2013). In dicots, all PM-susceptibility genes belong to Clade V (Consonni et al., 2006; Bai et al., 2008; Feechan et al., 2008; Winterhagen et al., 2008). In a previous contribution we identified three MLO genes of *M. domestica* up-regulated during early stages of PM infection (Pessina et al., 2014). Two of them, MdMLO11 and MdMLO19, belong to dicot clade V and MdMLO18 to clade VII. Because MLO genes outside clade V acting as S-genes are not known, only MdMLO11 and MdMLO19 were considered reasonable candidates to be knocked-down in apple.

MdMLO11 and MdMLO19 were knocked-down to assess their role in supporting apple susceptibility to PM. RNAi was adopted to reduce the expression of the two MLO genes, and in spite of the high number of transgenic 'Gala' lines generated (48), only for three of them a significant reduction of expression of the target genes was detected. In part, this was expected because short RNAi fragments of less than 150 bp, like those used in our experiments, are known for their limited knock-down efficiency. On the other hand, they have the advantage of being more specific, thus avoiding the generation of off-target silencing of other clade V MLO genes, as detected in our experiments.

In some species, knock-out or knock-down of MLO genes causes pleiotropic phenotypes, such as formation of necrotic spots on leaves and reduced grain yield in barley (Jorgensen, 1992), slow growth in *A. thaliana* (Consonni et al., 2006) and reduced plant size in pepper (Zheng et al., 2013). Such or other unexpected pleiotropic phenotypes were not observed under the greenhouse conditions specified in Materials and Methods.

Greenhouse inoculation of apple transgenic lines resulted in a statistically significant reduction of disease severity in lines TG11+19 and TG19. Because of the knock-down of MdMLO19 in both resistant lines, it was assumed that this was the most effective gene responsible for the reduction of PM susceptibility. The knock-down of MdMLO11 did not result in a significant reduction of susceptibility and even its knock-down in combination with MdMLO19 resulted in any additional reduction of susceptibility. The conclusion is that out of the two Clade V genes induced by PM in apple, only MdMLO19 is a functional S-gene. Also MdMLO18, the Clade VII gene inducible by *P. Leucotricha* inoculation, should not be considered a PM S-gene. Line TG0 was considered with the purpose of assessing the effect on susceptibility to PM of the insertion of a "target ineffective" RNAi construct. TG0 was obtained from a transfer that aimed to knock-down MdMLO19. In the line, a decrease of expression of MdMLO19 was recorded, although not significant, as well as a moderate non-significant reduction of PM susceptibility. It is concluded that the insertion of an "ineffective" RNAi construct may have functional relevance, but this cannot be statistically proved.

The precise mechanism through which the loss-of-function of MLO S-genes reduces susceptibility to PM pathogens is not completely clear yet. However, mlo resistance is known to be linked to secretory vesicles traffic (Miklis et al., 2007; Feechan et al., 2011) and to the formation of cell wall appositions called papillae (Consonni et al., 2006). Papillae consist in a callose matrix enriched in proteins and auto-fluorogenic phenolics (Vanacker et al. 2000) whose formation depends on actin-dependent endomembrane transport (Hückelhoven, 2014). Lines 'Gala', TG11+19 and TG19 were characterized by the presence of papillae at 3 dpi, but shape and dimensions were different in resistant and susceptible lines. Rapid papilla formation (Lyngkær et al., 2000), increased papilla size at attempted penetration sites (Stolzenburg et al., 1984) and different biochemical composition (Chowdhury et al., 2014), may explain the noted differences between effective and non-effective papillae. In mlo lines, particularly in TG19, the size of papillae was larger than in the control, supporting the hypothesis that larger dimensions increase the efficacy of the papilla. Chowdhury et al. (2014) have shown that the difference between effective and non-effective papillae lies in the higher concentration of callose, cellulose and arabinoxylan of the effective ones. This possibly reflects the observed differences in fluorescence between papillae of resistant and susceptible lines. As a matter of fact, MLO proteins are considered negative regulators of vesicle-associated and actin-dependent defense pathways (Panstruga, 2005), which, once under the control of the fungus, induce actin filaments to supply nutrients for the growing hyphae (Miklis et al., 2007). The data presented here support the view that in apple wild-types, after penetration the pathogen controls the transport of material to the cell-wall, changing the composition of the papillae and turning them into non-effective. A similar work carried out in grapevine (Pessina et al., unpublished) support this interpretation: compared to the control, mlo grapevine lines showed larger and less defined papillae, similar to those observed in mlo apple.

REFERENCES

Abbott J C, Barakate A, Pinçon G, Legrand M, Lapierre C, Mila I, Schuch W, Halpin C: *Simultaneous suppression of multiple genes by single transgenes. Down-regulation of three unrelated lignin biosynthetic genes in tobacco.* Plant Physiol 2002, 128(3): 844-853

Acevedo-Garcia J, Kusch S, Panstruga R: *Magical mystery tour: MLO proteins in plant immunity and beyond.* New Phytol 2014, 204(2):273-81

Angeli D, Puopolo G, Maurhofer M, Gessler C, Pertot I: *Is the mycoparasitic activity of Ampelomyces quisqualis biocontrol strains related to phylogeny and hydrolytic enzyme production?* Biological Control 2012, 63; 348-358

Bai Y, Pavan S, Zheng Z, Zappel N, Reinstädler A, Lotti C, De Giovanni C, Ricciardi L, Lindhout P, Visser R G F, Theres K, Panstruga R: *Naturally occurring broad-spectrum powdery mildew resistance in a Central American tomato accession is caused by loss of MLO function.* MPMI 2008, 21: 30-39

Bari R, Jones J D G: *Role of plant hormones in plant defense responses.* Plant Mol Biol, 2009, 69:473-488.

Botton A, Eccher G, Forcato C, Ferrarini A, Begheldo M, Zermiani M, Moscatello S, Battistelli A, Velasco R, Ruperti B, Ramina A: *Signaling pathways mediating the induction of apple fruitlet abscission.* Plant Physiol 2011, 155(1):185-208

Büschges R, Hollricher K, Panstruga R, Simons G, Wolter M, Frijters A, van Daelen R, van der Lee T, Diergaarde P, Groenendijk J, Topsch S, Vos P, Salamini F, Schulze-Lefert P: *The barley Mlo gene: a novel control element of plant pathogen resistance.* Cell 1997, 88(5):695-705

Campbell C L, Madden L V: *Introduction to plant disease epidemiology.* John Wiley and Sons 1990, New York. 532 pp.

Chen Z, Noir S, Kwaaitaal M, Hartmann A, Wu M J, Mudgil Y, Sukumar P, Muday G, Panstruga R, Jones A M: *Two seven-transmembrane domain MILDEW RESISTANCE LOCUS O proteins cofunction in Arabidopsis root thigmomorphogenesis.* Plant Cell 2009, 21:1972-1991.

Chowdhury J, Henderson M, Schweizer P, Burton R A, Fincher G B, Little A: *Differential accumulation of callose, arabinoxylan* and *cellulose in nonpenetrated versus* penetrated papillae on leaves of barley infected with *Blumeria graminis f. sp. Hordei*. *New Phytol* 2014, 204: 650-660

Consonni C, Humphry M E, Hartmann H A, Livaja M, Durner J, Westphal L, Vogel J, Lipka V, Kemmerling B, Schulze-Lefert P, Somerville S C, Panstruga R: *Conserved requirement for a plant host cell protein in powdery mildew pathogenesis*. *Nature Genetics* 2006, 38(6): 716-720.

Dufour M C, Fontaine S, Montarry J, Corio-Costet M F: *Assessment of fungicide resistance and pathogen diversity in Erysiphe necator using quantitative real-time PCR assays*. *Pest Manag. Sci.* 2011, 67, 60-69.

Feechan A, Jermakow A M, Torregrosa L, Panstruga R, Dry I B: *Identification of grapevine MLO gene candidates involved in susceptibility to powdery mildew*. *Funct Plant Biol* 2008, 35:1255-1266

Feechan A, Kabbara s, Dry I B: *Mechanisms of powdery mildew resistance in the Vitaceae family Mol Plant Pathology* 2011, 12(3):263-274

Hellemans J, Mortier G, De Paepe A, Speleman F and Vandesompele J: *qBase relative quantification framework and software for management and automated analysis of real-time quantitative PCR data*. *Genome Biol.* 2007, 8:R19

Hückelhoven R: *The effective papilla hypothesis*. *New Phytol* 2014, 204: 438-440

Joshi S G, Schaart J G, Groenwold R, Jacobsen E, Schouten H J, Krens F A: *Functional analysis and expression profiling of HcrVf1 and HcrVf2 for development of scab resistant cisgenic and intragenic apples*. *Plant Mol Biol* 2011, 75:579-591

Jørgensen J H: *Discovery, characterization and exploitation of Mlo powdery mildew resistance in barley*. *Euphytica* 1992, 63:141-152.

Ling D, Salvaterra P M: *Robust R T-qPCR data normalization: validation and selection of internal reference genes during post-experimental data analysis*. *PLoS One* 2011, 6:3.

Lyngkjǽr M F, Newton A C, Atzema J L, Baker S J: *The Barley mlo-gene: an important powdery mildew source*. *Agronomie* 2000, 20 745-756.

Madden L V, Hughes G, Van Den Bosch F: *The Study of plant disease epidemics*. APS press, St. Paul, 2007.

Miklis M, Consonni C, Bhat R A, Lipka V, Schulze-Lefert P, Panstruga R: *Barley MLO modulates actin-dependent and actin-independent antifungal defense pathways at the cell periphery*. *Plant Physiol* 2007, 144:1132-1143

Panstruga R: *Serpentine plant MLO proteins as entry portals for powdery mildew fungi*. *Biochem Soc Transact* 2005, 33(Pt 2):389-392

Parlevliet J E: *What is durable resistance, a general outline*. In *Durability of Disease Resistance*. Edited by Jacobs T H, Parlevliet J E. Dordrecht: Kluwer; 1993:23-29.

Pavan S, Jacobsen E, Visser R G F, Bai Y: *Loss of susceptibility as a novel breeding strategy for durable and broad-spectrum resistance*. *Mol Breed* 2010, 25:1-12.

Pavan S, Schiavulli A, Appiano M, Marcotrigiano A R, Cillo F, Visser R G F, Bai Y, Lotti C, Ricciardi L: *Pea powdery mildew er1 resistance is associated to loss-of-function mutations at a MLO homologous locus*. *Theor Appl Gen* 2011, 123:1425-1431

Pessina S, Pavan S, Catalano D, Gallotta A, Visser R G F, Bai Y, Malnoy M, Schouten H J: *Characterization of the MLO gene family in Rosaceae and gene expression analysis in Malus domestica*. *BMC genomics* 2014, 15:618

Pessina S, Lenzi L, Perrazzolli M, Campa M, Dalla Costa L, Urso S, Valé G, Velasco R, Salamini F, Malnoy M: *MLO genes Knock-down reduces susceptibility to powdery mildew in grapevine*. Unpublished Reinstädler A, Milner J, Czembor J H, Piffanelli P, Panstruga R: *Novel induced mlo mutant alleles in combination with site-directed mutagenesis reveal functionally important domains in the heptahelical barley Mlo protein*. *BMC Plant Biol* 2010, 10:31.

Stolzenburg M, Aist J R, Israel H W: *The role of papillae in resistance to powdery mildew conditioned by the ml-o gene in barley. I Correlative evidence*. *Physiological Plant Pathology* 1984, 25, 337-346

Turechek W W, Carroll J E, Rosenberger D A: *Powdery mildew of apple*. NY State Integrated Pest Management Program: Cornell University 2004 (www.nysipm.cornell.edu/factsheets/treefruit/diseases/pm/apple_pm.pdf).

Vanacker H, Carver T L W, Foyer C H: *Early $H_2O_2$ accumulation in mesophyll cells leads to induction of glutathione during hypersensitive response in the barley-powdery mildew interaction*. *Plant Physiology* 2000, 123: 1289-1300

Wightwick A, Walters R, Allinson G, Reichman S, Menzies N: *Environmental risks of fungicides used in horticultural production systems*. *Fungicides* 2010, Odile Carisse (Ed.), ISBN: 978-953-307-266-1

Winterhagen P, Howard S F, Qiu W, Kovacs L G: *Transcriptional up-regulation of grapevine MLO genes in response to powdery mildew infection*. *Am J Enol Vitic* 2008, 59:2

Zheng Z, Nonomura T, Appiano M, Pavan S, Matsuda Y, Toyoda H, Wolters A A, Visser R G F1, Bai Y: *loss of function in Mlo orthologs reduces susceptibility of pepper and tomato to powdery mildew disease caused by Leveillula taurica*. *PLoS One* 2013, 8(7):e70723

The invention claimed is:

1. A *Malus domestica* plant which is resistant to *Podosphaera leucotricha* comprising a non-natural modification introduced into its genome that results in:
   reduced transcription of a nucleic acid sequence of SEQ ID NO: 2 as compared to a *Malus domestica* plant that is not resistant to *Podosphaera leucotricha*,
   wherein the non-natural modification is in the nucleic acid sequence of SEQ ID NO: 2.

2. The *Malus domestica* plant of claim 1 wherein the non-natural modification results in gene silencing.

3. A seed, tissue, or plant part of the *Malus domestica* plant of claim 1, wherein the seed, tissue, or plant part comprises the modification that results in:
   reduced transcription of the nucleic acid sequence of SEQ ID NO: 2 as compared to a *Malus domestica* plant that is not resistant to *Podosphaera leucotricha*.

4. A method for obtaining a *Malus domestica* plant that is resistant to *Podosphaera leucotricha*, the method comprising modifying the *Malus domestica* plant by: reducing transcription of a nucleic acid sequence of SEQ ID NO: 2 as compared to a *Malus domestica* plant that is not resistant to *Podosphaera leucotricha*, wherein the reduction results from a non-natural modification in the nucleic acid sequence of SEQ ID NO: 2.

5. The method of claim 4, wherein the nucleic acid sequence of SEQ ID NO: 2 is silenced.

6. A *Malus domestica* plant produced from the method according to claim 4, wherein the plant has:
   reduced transcription of the nucleic acid sequence of SEQ ID NO: 2 as compared to a *Malus domestica* plant that is not resistant to *Podosphaera leucotricha*.

7. A seed, tissue, or plant part of the *Malus domestica* plant according to claim 6, wherein the seed, tissue, or plant part has:
   reduced transcription of the nucleic acid sequence of SEQ ID NO: 2 as compared to a *Malus domestica* plant that is not resistant to *Podosphaera leucotricha*.

* * * * *